United States Patent [19]

Berglund et al.

[11] 4,310,509

[45] Jan. 12, 1982

[54] PRESSURE-SENSITIVE ADHESIVE HAVING A BROAD SPECTRUM ANTIMICROBIAL THEREIN

[75] Inventors: Claire A. Berglund, Shoreview, Minn.; Paul D. Rosso, St. Joseph Township, St. Croix County, Wis.

[73] Assignee: Minnesota Mining and Manufacturing Company, St. Paul, Minn.

[21] Appl. No.: 62,363

[22] Filed: Jul. 31, 1979

[51] Int. Cl.$^3$ .................... A61K 9/70; A61F 13/00; A61L 15/03; A61K 33/18

[52] U.S. Cl. ........................................ 424/28; 424/80; 424/81; 424/78; 424/150; 128/155; 128/156; 128/268

[58] Field of Search ............... 424/28, 80, 81, 150; 128/155, 156, 268

[56] References Cited

U.S. PATENT DOCUMENTS

| | | |
|---|---|---|
| 2,400,389 | 5/1946 | Cavalito . |
| 2,427,022 | 9/1947 | Russ et al. ........................... 167/84 |
| 2,739,922 | 3/1956 | Shelanski ........................... 424/150 |
| 2,752,281 | 6/1956 | Niederhauser . |
| 2,826,528 | 3/1958 | Shelanski . |
| 2,853,417 | 9/1956 | Werner . |
| 2,927,914 | 3/1960 | Lee . |
| 2,951,766 | 9/1960 | White . |
| 3,028,300 | 4/1962 | Cantor et al. ....................... 424/150 |
| 3,028,300 | 4/1962 | Cantog et al. . |
| 3,307,544 | 3/1967 | Gander et al. . |
| 3,347,233 | 10/1967 | Migilarese . |
| 3,577,516 | 5/1971 | Gould et al. . |
| 3,579,628 | 5/1971 | Gander et al. . |
| 3,598,123 | 8/1971 | Zaffaroni ........................... 128/268 |
| 3,632,740 | 1/1972 | Robinson ........................... 424/28 |
| 3,645,835 | 7/1972 | Smith et al. . |
| 3,645,835 | 2/1972 | Hodgson . |
| 3,728,148 | 4/1973 | Pietsch et al. . |
| 3,734,097 | 5/1973 | Zaffaroni ........................... 128/268 |
| 3,749,772 | 7/1973 | Cardarelli ........................... 424/150 |
| 3,769,071 | 10/1973 | Trancik ........................... 117/122 P |
| 3,886,268 | 5/1975 | Halpern ........................... 424/80 |
| 3,896,789 | 7/1975 | Trancik ........................... 128/156 |
| 3,896,789 | 7/1975 | Trancik . |
| 3,898,326 | 8/1975 | Cantor et al. . |
| 3,907,720 | 9/1975 | Field et al. . |
| 3,969,498 | 7/1976 | Catania et al. . |
| 3,996,934 | 12/1976 | Zaffaroni . |
| 4,045,364 | 8/1977 | Richter . |
| 4,073,291 | 2/1978 | Marvel et al. ........................... 128/155 |
| 4,094,967 | 6/1978 | Gilbert ........................... 424/28 |
| 4,113,851 | 9/1978 | Leveen et al. ........................... 424/150 |
| 4,113,857 | 9/1978 | Shetty . |
| 4,147,775 | 4/1979 | Schwartz et al. ........................... 424/150 |
| 4,151,275 | 4/1979 | Cantor et al. ........................... 424/150 |

FOREIGN PATENT DOCUMENTS

| | | |
|---|---|---|
| 11471 | 12/1979 | European Pat. Off. . |
| 685805 | 12/1939 | Fed. Rep. of Germany . |
| 1925348 | 5/1969 | Fed. Rep. of Germany . |
| 2012584 | 3/1970 | France . |
| 1213295 | 11/1970 | United Kingdom . |
| 1471402 | 1/1974 | United Kingdom . |
| 1533406 | 11/1978 | United Kingdom . |
| 578971 | 7/1978 | U.S.S.R. . |

OTHER PUBLICATIONS

Chem. Abstracts 66 #88643h (1967) of Neth. Appl. 6,507,109.
Chem. Abstracts 77 #92889 (1972) of Ger. 1,593,155.
Chem. Abstracts 78 #106374a (1973) Aussems et al.
Chem. Abstracts 89 #36658x (1978) Knuutila et al.
Chem. Abstracts 78 #70235k (1973) of Ger. Off. 2,263,130.
Chem. Abstracts 82 #77112p (1975) of Ger. Off. 2,417,872.
Chem Abstracts 85 #14541u, #57405v #72841d (1976) Hegna.

Primary Examiner—Shep K. Rose
Attorney, Agent, or Firm—Cruzan Alexander; Donald M. Sell; Gary L. Griswold

[57] ABSTRACT

A composition and a process for making the same is provided wherein a chemical and storage stable pressure-sensitive adhesive has homogeneously dispersed therein a broad-spectrum antimicrobial agent. When the composition is placed in contact with the skin, it uniformly and controllably releases the broad-spectrum antimicrobial agent with substantially unaltered broad-spectrum antimicrobial activity.

11 Claims, No Drawings

PRESSURE-SENSITIVE ADHESIVE HAVING A BROAD SPECTRUM ANTIMICROBIAL THEREIN

This invention relates to a dermatologically acceptable composition made of a pressure-sensitive adhesive and a broad-spectrum antimicrobial agent uniformly dispersed therein which controllably releases from the composition when the composition is placed in contact with the skin.

Numerous pathogens are present on the human skin. In a hospital environment it is generally desired that the growth of disease-producing microorganisms be inhibited and preferably that these microorganisms be destroyed so as to control patient infection and encourage wound healing. As a result, the application to the skin surface of topical bactericidally active agents has become a standard part of the aseptic hospital technique.

The topical applications of broad-spectrum antimicrobials have been in the form of preoperative skin preps, surgical scrub tissues, e.g. U.S. Pat. No. 4,045,364, washes, wound cleaners, lotions and ointments. In some instances such a delivery is effective for the particular purpose for a limited period of time. Microorganisms that may have survived the initial application of the antimicrobial agent act as a seed causing the pathogen population in some instances to rise to their initial levels. Continuous application of an antimicrobial agent to the site is a means of inhibiting this increase in population.

While numerous biologically active agents have been incorporated into adhesive layers on a substrate to provide a continuous application to the body of the agent, there has been no incorporation of a broad-spectrum antimicrobial into an adhesive layer which has been characterized by stability and unaltered activity of the broad-spectrum antimicrobial. Examples of various other agents that have been incorporated into adhesives are U.S. Pat. No. 2,137,169 were phenol, thymol, methanol, etc. are added to a starch adhesive; U.S. Pat. No. 3,249,109 where benzocaine was added to a tacky gelatin; U.S. Pat. No. 3,632,740 where a corticosteroid is added to an adhesive; U.S. Pat. No. 3,734,097 where a microencapsulated anti-neoplastic agent is added to an adhesive; U.S. Pat. No. 4,073,291 where Tretinoin is added to an adhesive; U.S. Pat. No. 3,769,071 where 5-fluorouracil is incorporated into an adhesive; and U.S. Pat. No. 3,896,789 where retinoic acid is incorporated into a pressure-sensitive adhesive tape. Previous attempts at incorporating a broad-spectrum antimicrobial into the adhesives have been frustrated by uncontrollable release which causes skin irritation in some patients and failure to obtain sufficient antimicrobial activity.

The present invention is directed to a process for the formation of a storage stable pressure-sensitive adhesive composition and a composition which when placed in contact with skin uniformly and controllably releases the broad-spectrum antimicrobial agent with substantially unaltered activity. This is accomplished by the present invention with little or no skin irritation.

The term broad-spectrum is used herein to mean that the antimicrobial agent has activity against more than one type of microorganism, i.e. both gram positive and gram negative bacteria and would very likely also have activity against fungi and viruses (Reference: Federal Register, Vol. 39, No. 179).

The stable composition which results from the process of the present invention may be generally described as comprising a broad-spectrum antimicrobial agent and a dermatologically acceptable normally room temperature tacky pressure-sensitive adhesive (PSA) which is compatible with the antimicrobial agent. The PSA has an antiseptically active amount of the broad-spectrum antimicrobial agent homogeneously dispersed therein. By "homogeneously" it is meant that the broad-spectrum antimicrobial is distributed throughout the PSA, e.g. in uniform structure or composition, substantially in the manner that cream is dispersed in homogenized milk. This homogeneous dispersion in the present invention allows for continuous, uniform and controlled release of the antimicrobial when the composition is in contact with the skin.

The process of the present invention involves forming an emulsifiable concentrate or an organic solution concentrate of the broad-spectrum antimicrobial and mixing it into the adhesive such that the broad-spectrum antimicrobial is homogeneously dispersed as a separate phase throughout the adhesive medium.

Stated another way, the process of the present invention involves the formation of a broad-spectrum antimicrobial solution comprising a broad-spectrum antimicrobial agent and a solvent and of a normally room temperature tacky pressure-sensitive adhesive which is compatible with the previously selected broad-spectrum antimicrobial agent. The broad-spectrum antimicrobial solution and pressure-sensitive adhesive are then mixed so that the solution containing broad-spectrum antimicrobial agent is homogeneously dispersed in the pressure-sensitive adhesive. The homogeneous dispersion is then spread or coated to a substantially uniform layer. This wet layer is then dried in order to remove the solvents. The resulting composition is comprised of an antiseptically active amount of the broad-spectrum antimicrobial agent homogeneously and stably dispersed in the pressure-sensitive adhesive.

The antimicrobial solution is comprised basically of a broad-spectrum antimicrobial agent and a solvent. As stated above the term broad-spectrum is used herein to mean that the antimicrobial agent has activity against both gram positive and gram negative bacteria and would very likely also have activity against fungi and viruses. Examples of antimicrobial agents which exhibit this broad-spectrum activity are iodine, chlorhexidine and polyvinylpyrrolidoneiodine (PVP-I). The latter two broad-spectrum antimicrobial agents will be utilized herein to exemplify various aspects of the present process.

The antimicrobial agent solution is formed so as to contain approximately 1–50% by weight of a broad-spectrum antimicrobial agent and from approximately 99–50% by weight of a solvent. The final percentage selected is largely dependent on the solubility of the broad-spectrum anti-microbial agent utilized. For example, when polyvinylpyrrolidone (PVP-I) is utilized as the antimicrobial agent the solution preferably contains 35–40% by weight PVP-I and 65–60% by weight solvent.

The solvents used in the antimicrobial solution may be a single type of solvent or a combination of solvents such as water or water soluble solvents, e.g., methanol, ethanol, ethyl acetate, tetrahydrofuran, etc. The preferred solvent for PVP-I is either water or ethanol.

When the aforementioned PVP-I broad spectrum antimicrobial solution is incorporated into the pressure-sensitive adhesive, discussed below, the resulting PVP-I concentration in the final composition normally varies from 2-35% by weight. The optimum concentration of PVP-I on a solids basis will be approximately 10% (yielding 1% iodine). The upper limit of the concentration of PVP-I is determined by the maximum amount that may be contained without deleteriously affecting the adhesive properties of the adhesive. When chlorhexidine is used as the antimicrobially active agent, the antimicrobial solution comprises approximately 20 weight percent chlorhexidine diacetate and 80 weight percent solvent. The preferred solvent with chlorhexidine is denatured ethanol. The resulting final composition is normally 3-10 wt. % solid chlorhexidine.

The adhesive matrix is formed of a normally room temperature tacky pressure-sensitive adhesive which is chemically compatible with the previously selected broad-spectrum antimicrobial agent utilized in the broad spectrum antimicrobial solution.

Although it is generally believed that an acid medium renders many broad-spectrum antimicrobial agents more stable, it has been found that an acid adhesive is physically incompatible with antimicrobial agents such as PVP-I. The ultimate homogeneous distribution of broad-spectrum antimicrobial agent cannot be achieved in an acid adhesive so as to obtain controlled release without substantially altering the activity of the agent. Also when a broad-spectrum antimicrobial solution containing a broad-spectrum antimicrobial agent is mixed with a pressure-sensitive adhesive which is acidic in nature, a premature coagulation of the adhesive has been experienced. It therefore is preferred that broad-spectrum antimicrobial agents such as PVP-I or chlorhexidine be utilized with normally room temperature tacky adhesive mediums which are substantially free of acidic components to facilitate the homogeneous dispersion of the broad-spectrum antimicrobial without the negative alteration to the activity of the antimicrobial agent. By "substantially free of acidic components" it is meant that the pressure-sensitive adhesive be substantially free of substituent groups which exhibit acid functionality, e.g. acrylic acid groups etc. Classes of such room temperature tacky pressure-sensitive adhesives which are or can be rendered substantially free of acidic components include polyacrylates, polyolefins, silicone adhesives, polyvinyl ethers, polyesters, polyurethanes, etc. as well as selected copolymers thereof. The formulation of these adhesives are well known in the art, e.g. U.S. Pat. Nos. RE 24906, 2,973,286, 3,307,544, 3,645,835, etc. The actual choice of the pressure-sensitive adhesive is largely dependent on the end use to which the artisan will apply the final composition and the broad-spectrum antimicrobial agent that is to be incorporated therein. It will be appreciated by one skilled in the art that the aforestated adhesive components might also include various chemical modifiers so as to enable them to have the utility dictated by the situation, e.g. tackifiers, crosslinkers, stabilizers, initiators, etc.

If a solvent is needed for use with the pressure-sensitive adhesive, the solvent should be chosen to be compatible with the broad-spectrum antimicrobial solution, e.g. with acrylic adhesives and chlorhexidine, a polar solvent could be utilized. The solvent of the adhesive solution for use with PVP-I preferably should be capable of solubilizing the solvent of the antimicrobial solution while at the same time being a non-solvent for the broad-spectrum antimicrobial agent.

After formation, the broad-spectrum antimicrobial solution and the pressure-sensitive adhesive are mixed such that the broad-spectrum antimicrobial solution is homogeneously dispersed in the pressure-sensitive adhesive. The mixing is performed at room temperature and may be accomplished utilizing a spatula or when necessary and apparatus which results in a shearing type mixing action, e.g. a Dispersator ® sold by Premier Mill Corp., Temple, Pa. It is believed that this mixing results in the broad-spectrum antimicrobial solution forming either a stable water-in-oil emulsion or a dispersed microfine phase in the second solution. For example, when 22 parts by weight of the broad spectrum antimicrobial solution comprising a 35% by weight broad-spectrum antimicrobial agent such as PVP-I, in water containing a non-ionic surfactant (discussed below) is mixed with 78 parts by weight of a 44% solid adhesive solution, a very stable water-in-oil emulsion is formed wherein the dispersed phase consists of stable discrete water droplets averaging about 10 microns in diameter. Alternatively, when the antimicrobial solution comprised of a broad-spectrum antimicrobial agent as PVP-I in an organic solvent containing a surfactant is mixed with the adhesive, it is believed that the solvent of the adhesive extracts the solvent of the antimicrobial solution causing the broad-spectrum antimicrobial in the form of PVP-I to separate out as a distinct minute separate phase of PVP-I particles. The presence of the non-ionic surfactant stabilizes the discrete second phase of PVP-I as microfine particles homogeneously dispersed in the adhesive. In some instances, certain adhesives appear to function as the surfactant and stabilize the PVP-I dispersion.

The homogeneous dispersion from above may then be spread or coated by means known to the art onto various backings to form dressings, drapes, tapes, etc. The preferred backing material for use with the present invention is a polyethylene film. This coating can be done by forming a substantially uniform layer of the homogeneous dispersion onto a release liner which facilitates the composition's later attachment to other substrates. Alternatively, the uniform layer of the homogeneous dispersion may be formed directly on to a flexible substrate thus eliminating the need for the release liner. The uniform layer of the homogeneous dispersion is ten dried resulting in a composition which contains an antiseptically active amount of the broad-spectrum antimicrobial agent homogeneously and stably dispersed in the pressure-sensitive adhesive and capable of releasing the same when brought in contact with skin. By "stably" it is meant that a composition coating of 11 grains per 24 sq. in. on a polyethylene backing can be exposed to a temperature of 120° F. at a relative humidity of 9% for two (2) weeks or to a dose of 2.5 megarads of gamma irradiation without substantial alteration of the physical appearance or of the chemical activity as tested by the starch test. Alternatively, microbiological activity of the composition can be tested by Zone inhibition Assay which is described in detail below.

The starch test is performed by preparing an indicator solution. A drop of the Paragon Indicator solution is placed on the adhesive surface. Formation of blue coloration in the drop indicates availability of iodine.

The indicator solution is prepared by dissolving 62.5 g of Paragon Iodine Titration Indicator (Eastern Chemical, Division of Guardian Chemical Corp., Hauppauge, N.Y.) in 250 ml of distilled water with stirring.

As stated briefly above, a surfactant may comprise approximately 0-5% of the antimicrobial solution in order to stabilize the broad-spectrum antimicrobial. The surfactants used in the antimicrobial solution may have a wide variety of structures and a wide variety of physical properties such as are characterized by the hydrophilelipophile balance (HLB). Non-ionic surfactants preferably have a HLB value from 4 to 14. Suitable non-ionic surfactants include: Triton ® X-100 (sold by Rohm & Haas, Philadelphia, Pa.) which is an ethylene oxide adduct of octyl phenol. Another useful surfactant is sold is Pluronics brand surfactants by Wyandotte Chemical Company of Wyandotte, Mich., which are condensates of ethylene oxide with hydrophobic bases formed by condensing propylene oxide with propylene glycol.

The invention is further illustrated by the following nonlimiting examples:

EXAMPLE 1

2-ethylhexylacrylate/N-vinylpyrrolidone adhesive (90/10 weight percent) was synthesized as follows:

86.4 g. ethyl acetate, 0.88 g. ethanol, 77.3 g. heptane, 11.0 g. N-vinylpyrrolidone, 99.0 g. 2-ethylhexyl acrylate, and 0.294 g. azobisisobutyronitrile were charged to a one pint bottle. The bottle was flushed with a stream of nitrogen for 3-4 minutes, sealed, and tumbled in a water bath at 55° C. for 20 hours. The (non-volatile) solids of the solution were 39.4%. The inherent viscosity, measured in ethyl acetate at 30° C. with a #50 Cannon-Fenske viscometer, was 0.735.

Next, 24.6 g. of a stock solution of a 35 wt. % polyvinylpyrrolidone-iodine complex (PVP-I) water solution was placed into a 100 ml wide-mouth bottle, to which was then added 0.86 g. of an ethylene oxide adduct of octyl phenol sold by Rohm & Haas as Triton ® X-100. This surfactant/PVP-I solution was added to a bottle containing 73.1 g. of the previously synthesized 2-ethylhexylacrylate/N-vinylpyrrolidone adhesive. The resulting composition was stirred with a spatula to obtain a uniform dispersion. A uniform coating was applied to a release liner using a 6" knife coater. The coating was then dried in a 200° F. oven. The dried film was then laminated to a 1½ mil corona and quaternary amine antistat treated polyethylene film.

EXAMPLE 2

6.6 g of a 45% PVP-I ethanol solution was added to a bottle containing 26.0 g. of the 2-ethylhexylacrylate/N-vinylpyrrolidone adhesive from Example 1. This formulation was stirred with a microspatula to obtain a uniform dispersion. The coating/laminating procedure was the same as in Example 1. In Examples 1 and 2 small amounts of polyvinylpyrrolidone may be incorporated into the adhesive either as a physical mix or as an integral part of the adhesive so as to increase the compatibility of the PVP-I with the adhesive.

EXAMPLE 3

Preparation of an antimicrobial adhesive with Monsanto Gelva adhesives:

First a 80/20 blend of Monsanto Gelva adhesives containing 133.3 g. of 30% solids Gelva RA 737 having a $\overline{M}_n$ of 70,800 and $\overline{M}_w$ of 722,900 and 22.7 g. of 44% solids Gelva RA 788 having a $\overline{M}_n$ of 77,350 and a $\overline{M}_w$ of 493,000 was prepared. The 80/20 Gelva blend 37.5 g. was placed in a bottle containing 6.6 g. of 45% by weight PVP-I in EtOH. The formulation was stirred with a microspatula to obtain a uniform dispersion. The coating/laminating procedure was the same as Example 1.

EXAMPLE 4

The biological activity of Example 1, 2, and 3 was determined by a Zone of Inhibition test utilizing the following procedure: The assay bacterium *Bacillus subtilis* was grown in rotary shake culture (200 rpm) for approximately 6 hours at 37° C. The growth medium, L-broth, consisted of the following ingredients dissolved in 1 L of distilled water and adjusted to pH 7.0: tryptone 10 g, yeast extract 5 g sodium chloride 10 g, glucose 1 g. This culture was diluted in sterile L-broth to 50% T @ 660 mu, further diluted 1:10, and inoculated at a ratio of 1:100 into molten soybean-casein digest agar medium (Inolex) maintained at 45°–50° C. Assay plates were prepared by first pipesetting a 5 ml base layer of soybean-casein digest agar medium (TSA), allowing this to harden at room temperature in disposable petri dishes, and then overlaying with 5 ml of seeded TSA. These preparations were used the same day. The previously coated polyethylene films from Example 1, 2 and 3 were tested in the same way regardless of the antimicrobial incorporated into the adhesive layer. Ten 6 mm discs were cut from an evenly coated area (ie no visible flaws) with a heavy duty paper punch (Master Products, Series 25). The paper backing was removed from the coated disc with the aid of forceps and microspatula. The coated disc was then placed adhesive-side down on the seeded-agar surface, 4 per plate.

Reference discs were prepared differently depending on the antimicrobial agent. Aqueous solutions of chlorhexidine acetate ranging from 0.01 percent to 0.25 percent (w/v) were used to prepare discs containing 1 ug to 25 ug each from 10 ul aliquots applied to 6 mm filter paper discs (S and S No. 740-E).

Iodine reference disc were then prepared. A solution containing 10 percent iodine was prepared by dissolving 1 g of iodine and 1 g of sodium iodide in 10 percent aqueous acetone using a 10 ml volumetric flask. This stock solution, freshly prepared, and the same solvent were used to prepare 0.25, 0.5, 0.75, and 1.0 percent iodine solutions. From these dilutions, 10 ul aliquots were applied to 6 mm polyester fabric discs placed on the seeded agar surface to provide discs containing 25, 50, 75, 100 ug iodine each. (The polyester fabric was leached overnight in solvent to remove inherent antibacterial activity prior to punching). Each reference disc was covered with a 1 inch square of 2-ml polyethylene to prevent vaporization prior to diffusion through the underlying agar.

The coated discs and reference disc assay plates were incubated overnight at room temperature. Zones of inhibition around the discs were measured to the nearest 0.5 mm with the aid of a binocular stereoscopic microscope. In the case of iodine antimicrobials, the coated discs were also removed to examine plates for areas of growth inhibition under the discs.

Assay results for reference antimicrobials using the preceding methods demonstrate that the diameter of the zone of inhibition measured in mm is linearly proportional to $LOG_{10}$ concentration for each ageant over the range examined. The release of antimicrobial from the adhesive of the present invention can be estimated by graphic interpolation of the inhibition values.

The biological activity (from zone of inhibition) for antimicrobial adhesives of Examples 1, 2 and 3 were all positive (19–30 micrograms of iodine per 6 mm disc) which is 90–100% of the total iodine charged.

In vivo efficacy on seeded human skin is exhibited by a 4–5 log reduction of Staphylococcus aureus and Psudomonas aeruginosa after one hour.

EXAMPLE 5

A formulation was prepared as follows:

| | |
|---|---|
| Gelva adhesive RA-737 (about 30% solids having a $\overline{M}_n$ of about 70,800 and a $\overline{M}_w$ of about 722,900) | 480 g. |
| Gelva adhesive RA-788 (about 40% solids having a $\overline{M}_n$ of about 77,350 and a $\overline{M}_w$ of about 493,000) | 90 g. |
| A solution containing 20 wt% chlorhexidine acetate (Imperial Chemical Industries, Ltd.) in denatured ethanol | 27 g. |
| Additional denatured ethanol solvents | 50 g. |

The formulation was stirred at room temperature to yield a uniform solution of 3 wt % chlorhexidine acetate on adhesive solids. This solution was coated on silicone release liner and dried to form a clear homogeneous adhesive film of coating weight equal to 11 grains/24 sq. in. The adhesive film was laminated to a backing of a corona and quaternary amine antistat treated polyethylene film to form a composite construction containing the antimicrobial chlorhexidine acetate. The composite construction exhibited in vivo efficacy on seeded human skin of a one log reduction of Staphylococcus aureus and of Pseudomonas aeruginosa after one hour. No skin irritation was observed from the use of this composition.

What is claimed is:

1. A process for making a dermatologically acceptable composition which controllably releases an antiseptically active broad-spectrum antimicrobial agent when placed in contact with skin comprising forming a solution of a broad-spectrum antimicrobial agent; forming a room temperature tacky pressure-sensitive adhesive which is compatible with said broad-spectrum antimicrobial agent; mixing said antimicrobial agent solution and said pressure-sensitive adhesive such that the broad-spectrum antimicrobial agent from said antimicrobial agent solution is homogeneously dispersed in said pressure-sensitive adhesive; and drying said homogeneous dispersion so as to remove said solvents leaving an antiseptically active amount of said broad-spectrum antimicrobial agent homogeneously and stably dispersed in said pressure-sensitive adhesive.

2. The process of claim 1 which includes the additional step of introducing a surfactant into said antimicrobial agent solution prior to mixing with said pressure-sensitive adhesive.

3. A composition which releases an antiseptically active broad-spectrum antimicrobial when placed in contact with skin comprising an antiseptically active amount of a broad-spectrum antimicrobial agent and a dermatologically acceptable room temperature tacky pressure-sensitive adhesive which is chemically compatible with said broad-spectrum antimicrobial, said broad-spectrum antimicrobial agent being homogeneously and stably dispersed in said pressure-sensitive adhesive.

4. The composition of claim 3 wherein said antiseptically active broad-spectrum antimicrobial agent is chlorhexidine.

5. The composition of claim 3 wherein said antiseptically active broad-spectrum antimicrobial agent is polyvinylpyrrolidone-iodine complex.

6. A flexible backing material having attached thereto a composition which releases an antiseptically active broad-spectrum antimicrobial agent when placed in contact with skin comprising an antiseptically active amount of a broad-spectrum antimicrobial agent and a dermatologically acceptable room temperature tacky pressure-sensitive adhesive which is chemically compatible with said broad-spectrum antimicrobial agent, said antimicrobial agent being homogenously and stably dispersed in said pressure-sensitive adhesive.

7. The flexible backing material of claim 6 wherein said antiseptically active broad-spectrum antimicrobial agent is chlorhexidine.

8. The flexible backing material of claim 6 wherein said antiseptically active broad-spectrum antimicrobial agent is polyvinylpyrrolidone-iodine complex.

9. The flexible backing material and composition of claim 6 in the form of a drape.

10. The flexible backing material and composition of claim 6 in the form of a tape.

11. The flexible backing material and composition of claim 6 in the form of a dressing.

* * * * *